United States Patent [19]

Liebetruth et al.

[11] 4,193,001
[45] Mar. 11, 1980

[54] TOMOGRAPHIC APPARATUS FOR PRODUCING TRANSVERSE LAYER IMAGES

[75] Inventors: Reiner Liebetruth; Norbert Mika, both of Erlangen, Fed. Rep. of Germany

[73] Assignee: Siemens Aktiengesellschaft, Berlin & Munich, Fed. Rep. of Germany

[21] Appl. No.: 934,167

[22] Filed: Aug. 16, 1978

[30] Foreign Application Priority Data

Sep. 16, 1977 [DE] Fed. Rep. of Germany ....... 2741732

[51] Int. Cl.² .............................................. A61B 6/02
[52] U.S. Cl. .................................................. 250/445 T
[58] Field of Search .................................... 250/445 T

[56] References Cited
U.S. PATENT DOCUMENTS 4,055,767 10/1977 Allemand ......................... 250/445 T
4,145,610 3/1979 Perilhou ........................... 250/445 T Primary Examiner—Alfred E. Smith
Assistant Examiner—T. N. Grigsby
Attorney, Agent, or Firm—Hill, Van Santen, Steadman, Chiara & Simpson

[57] ABSTRACT

A computer-tomograph having a fan-shaped x-ray beam and two detector arrays. The two detector arrays are arranged in parallel with one another and side by side. Their lengths are dimensioned such that one detector array is suited for the area of the head and the second is suited for the area of the trunk of the patient. The total number of detectors of the detector arrays is the same, so that the resolution of the shorter detector array is finer than that of the longer one. In each case, two corresponding detectors of the respective rows are connected in parallel to an input of the measured value converter.

5 Claims, 3 Drawing Figures

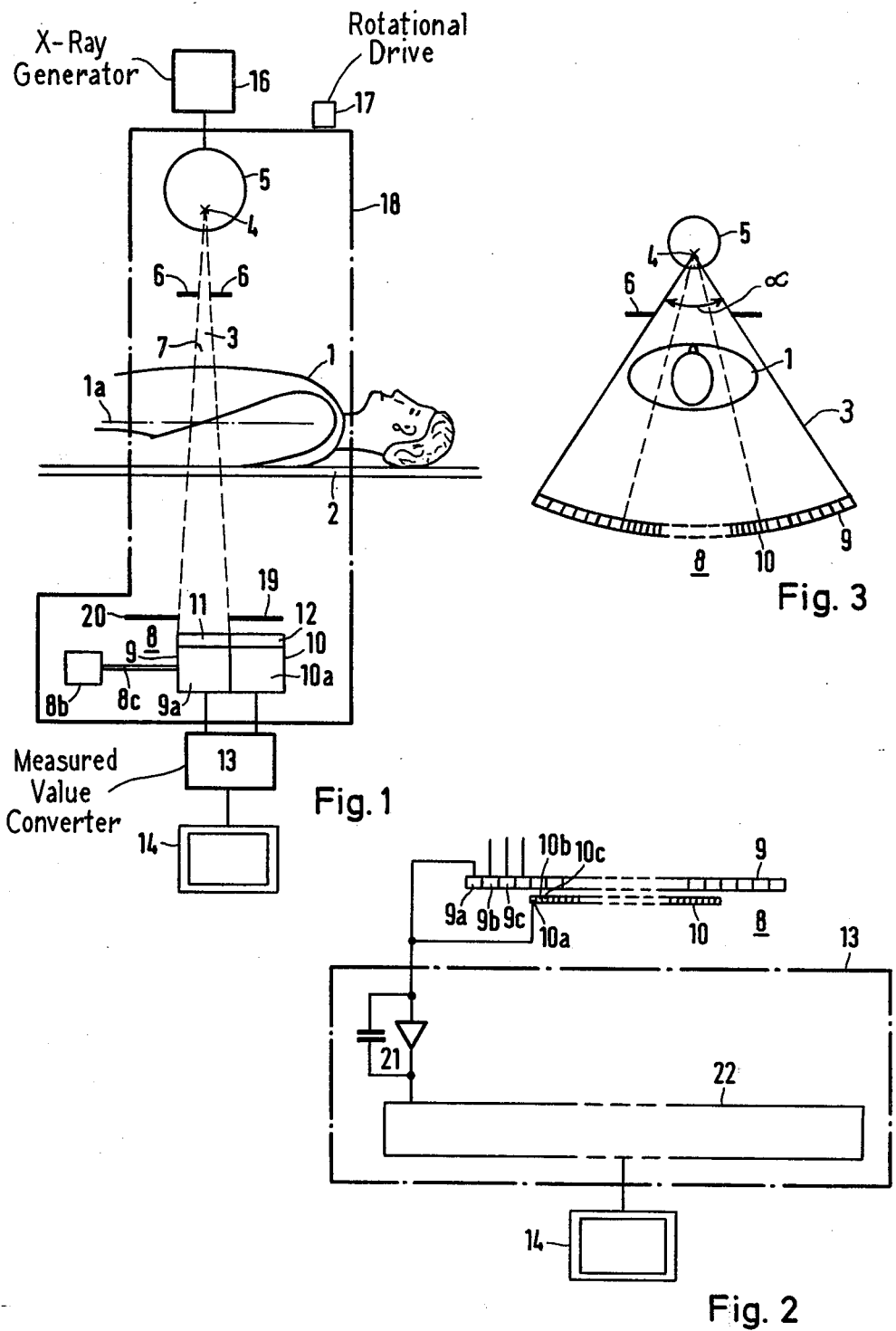

TOMOGRAPHIC APPARATUS FOR PRODUCING TRANSVERSE LAYER IMAGES

BACKGROUND OF THE INVENTION

The invention relates to a tomograph for producing transverse layer images of a radiography subject, having a radiation measuring arrangement comprising a radiation source producing a fan-shaped radiation beam which penetrates the radiography subject, whose cross-sectional extent perpendicular to the layer plane equals the layer thickness and in the layer plane is so great that the entire radiography subject is penetrated, and also a radiation receiver which determines the intensity of radiation behind the subject, and also having a rotating device for the measuring arrangement for the purpose of irradiating the radiography subject from different directions, and having a measured value converter for transforming the signals supplied by the radiation receiver into a layer image, wherein the radiation receiver consists of a number of individual detectors.

There is known a tomograph of this type, where the radiation receiver consists of one single row of detectors. The number of detectors in the row of detectors is selected in accordance with the desired image resolution. The measuring arrangement is rotated through an angle of 360° for the purpose of generating the input signals of the measured value converter. A tomograph of this description is suited as a so-called whole body scanner for the purpose of taking any desired transverse layer images of a patient. The length of the row of detectors must be dimensioned such that the x-ray beam detected by it completely penetrates each body layer to be reproduced.

The known tomograph has the disadvantage that when reproducing a body layer which is substantially smaller than the largest body layer, for example a cross section through the neck or the head of the patient, only a small number of detectors is active in producing the input signals of the measured value converter. The local resolution thus becomes smaller in relation to the size of the body layer to be reproduced.

SUMMARY OF THE INVENTION

The object underlying the invention is to construct a tomograph of the type initially described such that a good local resolution is provided within a wide range of sizes of the body layer to be reproduced.

This object is achieved according to the invention in that the radiation receiver has two or more rows of detectors arranged in parallel with one another and side by side, each of which is assigned to a specific area of the body, its length corresponding to the maximum width of the associated body region, in that the number of detectors per unit of length of a row of detectors is greater the shorter the row of detectors, and in that there is a control device for the radiation receiver which enables the selective detection of the x-ray beam by the desired row of detectors. With a tomograph according to the invention, a short and a long row of detectors may, for example, be provided whose total number of detectors is the same. The short row of detectors can serve to reproduce a cross section through the neck or the head of the patient and thereby offers a good local resolution owing to the finer graduation. The long row of detectors can serve in the generation of transverse layer images in the area of the trunk of a patient.

The invention is explained in greater detail in the following by means of an embodiment depicted in the accompanying sheet of drawings; and other objects, features and advantages will be apparent from this detailed disclosure and from the appended claims.

BRIEF DESCRIPTION OF THE DRAWINGS

FIG. 1 is a diagrammatic longitudinal view illustrating a tomograph according to the invention;

FIG. 2 shows a diagrammatic plan view of the radiation receiver of the tomograph according to FIG. 1 in conjunction with the associated measured value converter; and FIG. 3 shows a diagrammatic lateral view of the measuring arrangement for the tomograph according to FIG. 1.

DETAILED DESCRIPTION

In the case of the tomograph according to FIG. 1, a patient 1 is positioned on a couch 2 and is irradiated by a fan-shaped x-ray beam 3 (see FIG. 3 as to the fan-shaped configuration). The x-ray beam 3 emanates from the focus 4 of an x-ray tube 5 and is delineated (diaphragmed-in) by a primary radiation collimator 6 such that its cross-sectional extent perpendicular to the examined body layer 7 equals the layer thickness and in the examined body layer 7 is so great that the whole patient 1 is penetrated. Seen in the direction of radiation after the patient, there is arranged a radiation receiver 8 consisting of two rows of detectors 9 and 10 which are arranged in parallel with one another and side by side. A collimator is arranged in front of each of the detectors 9a, 9b, etc., and 10a, 10b, etc., of the rows of detectors 9 and 10. The collimators 11 and 12 of the detectors 9a and 10a are schematically illustrated in FIG. 1.

For the purpose of scanning the patient 1, for example the layer 7, the measuring arrangement 5, 8 is rotated through 360° about the patient 1, the axis of rotation being indicated at 1a. The scanning can take place in such a way, for example, that the x-ray tube 5, which is fed by an x-ray generator 16, is pulsed once per angular degree of rotation so that, for example, with 256 detectors per row of detectors, for one scanning operation 256×360 measuring signals are supplied to a measured value converter 13. Rotation takes place by means of a rotational drive device 17 which rotates a mounting frame 18 with the measuring arrangement 5, 8. The measured value converter 13 comprises a computer which calculates an image of the irradiated body layer from the measured value signals. For the purpose of reproducing this image, the measured value converter 13 is connected with a monitor 14.

During one rotation of the measuring arrangement 5, 8, the measuring signals are supplied in each case by only one of the rows of detectors 9 or 10. In the example, the row of detectors 9 supplies the measuring signals while the row of detectors 10 lies behind a collimator 19 which is impervious to radiation. If the row of detectors 10 is to be utilized to produce the measuring signals, then it is drawn into the x-ray beam 3 by a control device 8b, for example an electromagnet, via a rod 8c. The row of detectors 9 then lies behind a collimator 20 which is impervious to radiation.

FIG. 2 shows that the graduation of the row of detectors 10 is finer than the graduation of the row of detectors 9. In the example, the total number of detectors of each row of detectors 9, 10 is the same and in each case the corresponding detectors of the rows of detectors 9, 10 are connected in parallel to an integrator of the measured value converter 13. In FIG. 2, this is shown only for the detectors 9a and 10a. These detectors are connected to an integrator 21. There is assigned to each of the 256 input channels of a computer 22 in the example, an integrator to which there are connected two detectors respectively. The integrators hold the output signal of the respective detector until it is taken over by the computer 22 and then the integrators are reset to zero. Interrogation of the output signals of the integrators is carried out by the computer 22 in such a way that the output signals of the integrators are read out consecutively. Each input signal for one integrator originates in each case from only one detector, since in each case only one row of detectors according to FIG. 1 detects and measures the x-radiation issuing from the patient 1.

FIG. 3 clearly shows that the lengths of the rows of detectors 9 and 10 correspond to the dimensions of the associated areas of the body. The row of detectors 9 is here assigned to the trunk of the patient 1; that is, to a comparatively wide body layer, while the row of detectors 10 is assigned to the neck and head area of the patient 1; that is, to a comparatively narrow body layer. Within the framework of the invention, the collimator 6 can be constructed such that it adjusts the angle of aperture $\alpha$ of the x-ray beam to the row of detectors used for measuring in each case; that is, during the change-over from the row of detectors 9 to the row of detectors 10, the collimator 6 is adjusted to reduce said angle of aperture $\alpha$, FIG. 3, correspondingly.

It is conceivable, within the framework of the invention, when using straight rows of detectors, that the rows of detectors for example be mounted in angularly offset relation on frame 18, the rows of detectors 9 and 10 lying in a common plane but being offset by an angle of 90° or more and, such that by rotating the radiation receiver relative to frame 18, the row of detectors which is to be active in each case can be brought into the x-ray beam. Thus, a collimator can be provided on the frame which automatically shields the row of detectors not serving the purpose of measuring.

FIGS. 2 and 3 show that the number of detectors per unit of length of a row of detectors is greater the shorter the row of detectors. As a result, the local resolution in the case of narrow body layers which are examined with the row of detectors 10 is greater than in the case of wide body layers which are examined with the row of detectors 9.

It will be apparent that many modifications and variations may be effected without departing from the scope of the novel concepts and teachings of the present invention.

We claim as our invention:

1. Tomographic apparatus for producing transverse layer images of a radiography subject, having a radiation measuring arrangement comprising a source of radiation producing a fan-shaped radiation beam which penetrates the radiography subject, whose cross-sectional extent perpendicular to the layer plane equals the layer thickness and in the layer plane is so great that the whole radiography subject is penetrated, and also a radiation receiver which determines the intensity of radiation behind the subject, and also having a rotating device for the measuring arrangement for the purpose of irradiating the radiography subject from different directions, and having a measured value converter for transforming the signals supplied by the radiation receiver into a layer image, where the radiation receiver consists of a number of individual detectors, characterized in that the radiation receiver (8) has two or more rows of detectors (9, 10), each of which is assigned to a specific area of the body, the length of each row of detectors (9, 10) corresponding to the associated area of the body, in that the number of detectors per unit of length of said rows of detectors (9, 10) is greater the shorter the length of the row of detectors (9, 10), and in that there is a control device (8b, c) for the radiation receiver (9) which enables the x-ray beam to be detected selectively by one of said rows of detectors (9, 10) respectively.

2. Apparatus according to claim 1, characterized in that the control device (8b, c) is constructed such that it mechanically moves one row of detectors (9, 10) at a time into the x-ray beam (3).

3. Apparatus according to claim 1, characterized in that the number of detectors of all the rows of detectors (9, 10) is the same.

4. Apparatus according to claim 3, characterized in that in each case, respective corresponding detectors (9a, 9b; 10a, 10b, etc.) of each of the rows of detectors (9, 10) are connected in parallel to the measured value converter (13).

5. Apparatus according to claim 1, characterized in that there is a collimator (19, 20) which is impervious to radiation, which in each case shields the row of detectors (9, 10) not being used for measuring.

* * * * *